United States Patent [19]

Mattchen

[11] Patent Number: 4,583,531
[45] Date of Patent: Apr. 22, 1986

[54] HAND-HELD PULSATING JET LAVAGE

[75] Inventor: Terry M. Mattchen, 15254 Knapp St., Sepulveda, Calif. 91343

[73] Assignee: Terry M. Mattchen, Van Nuys, Calif.

[21] Appl. No.: 585,568

[22] Filed: Mar. 2, 1984

[51] Int. Cl.⁴ ............................................. A61H 9/00
[52] U.S. Cl. ..................................................... 128/66
[58] Field of Search .......................... 128/65, 66, 62 A; 604/33, 67, 131; 433/80; 239/99, 101, 102, 380, 381

[56] References Cited

U.S. PATENT DOCUMENTS

| | | | |
|---|---|---|---|
| 2,781,154 | 2/1957 | Meredith | 128/66 |
| 3,227,158 | 1/1966 | Mattingly | 128/66 |
| 3,393,673 | 7/1968 | Mattingly | 128/66 |
| 3,425,410 | 2/1969 | Cammack | 128/66 |
| 3,883,074 | 5/1975 | Lambert | 128/66 |
| 3,993,054 | 11/1976 | Newman | 128/66 |
| 4,215,476 | 8/1980 | Armstrong | 433/80 |
| 4,278,078 | 7/1981 | Smith | 128/66 |

OTHER PUBLICATIONS

Gross, Cutright, and Bhasker, entitled "Effectiveness of Pulsating Water Jet Lavage in Treatment of Contaminated Crushed Wounds", The American Journal of Surgery, Sep. 1972, vol. 124, pp. 373-377.
Amstutz, "Femoral Looseness in THR Using Conventional Cement Techniques," Orthopaedic Review, May 1980, vol. IX, No. 5, pp. 33-37.
Sherman, Byrick, Kay, Sullivan, and Waddell, entitled "The Role of Lavage in Preventing Hemodynamic and Blood-Gas Changes During Cemented Arthroplasty," The Journal of Bone and Joint Surgery, Inc., Apr. 1983, vol. 65-A, No. 4, pp. 500-505.

Primary Examiner—Gene Mancene
Assistant Examiner—Cary E. Stone
Attorney, Agent, or Firm—Nilsson, Robbins, Dalgarn, Berliner, Carson & Wurst

[57] ABSTRACT

A hand-held pulsating jet lavage is shown having a hand-held housing that may be separately sterilized from a disposable pump cartridge which has been sterilized prior to use by gamma radiation or ethylene oxide gas light. The disposable pump may be easily inserted into a pump chamber where a pump flange is positively engaged by a notch on the end of the housing motor. Closure of the chamber locks the pump into its desired position. A rigid tube extends from the pump to its nozzle to assure that a stream of sterile irrigation fluid is delivered to a surgical site with a pulse stream that has a sharp turn on, cut off interface between pulses.

41 Claims, 9 Drawing Figures

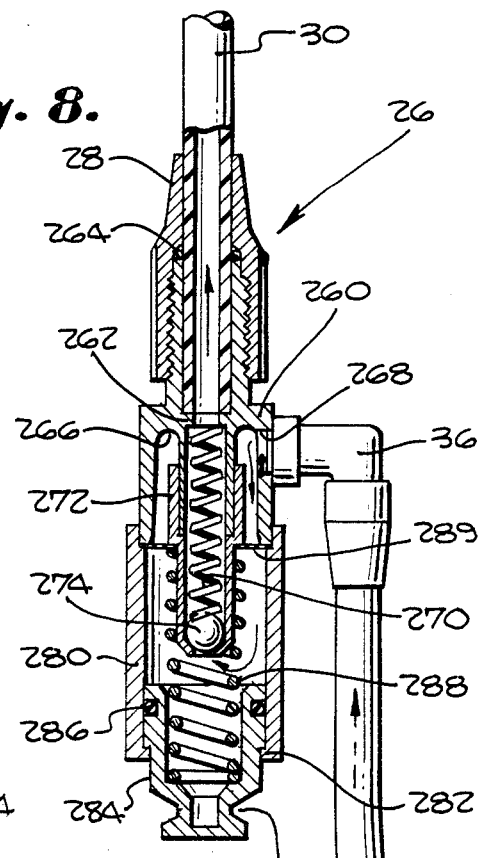
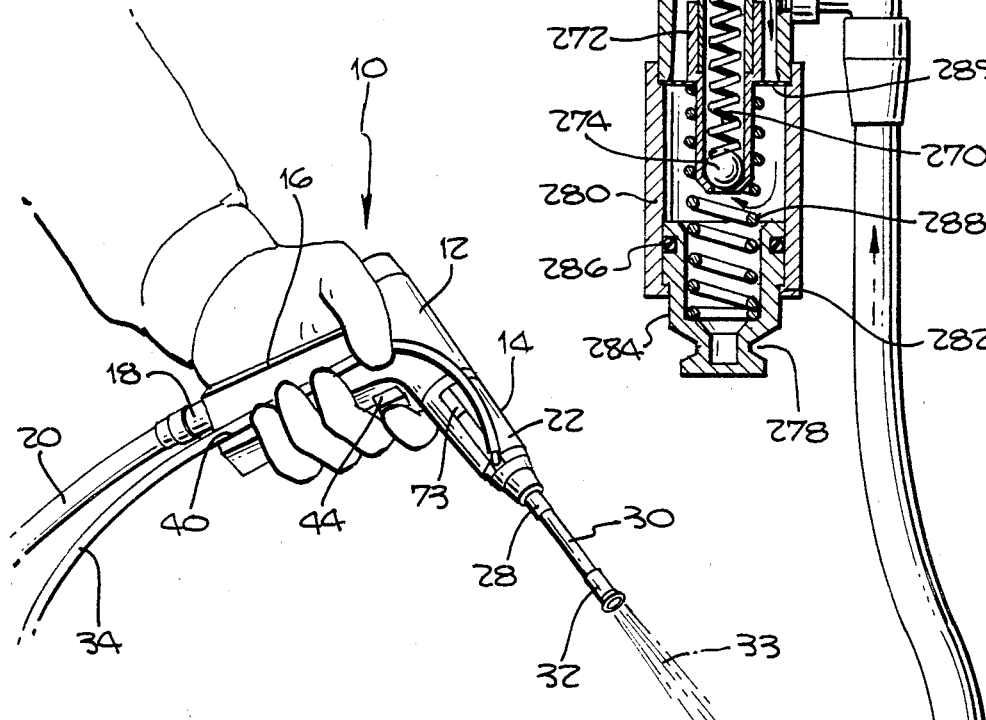
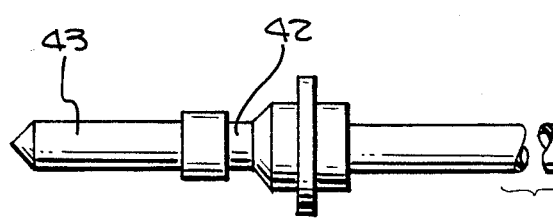

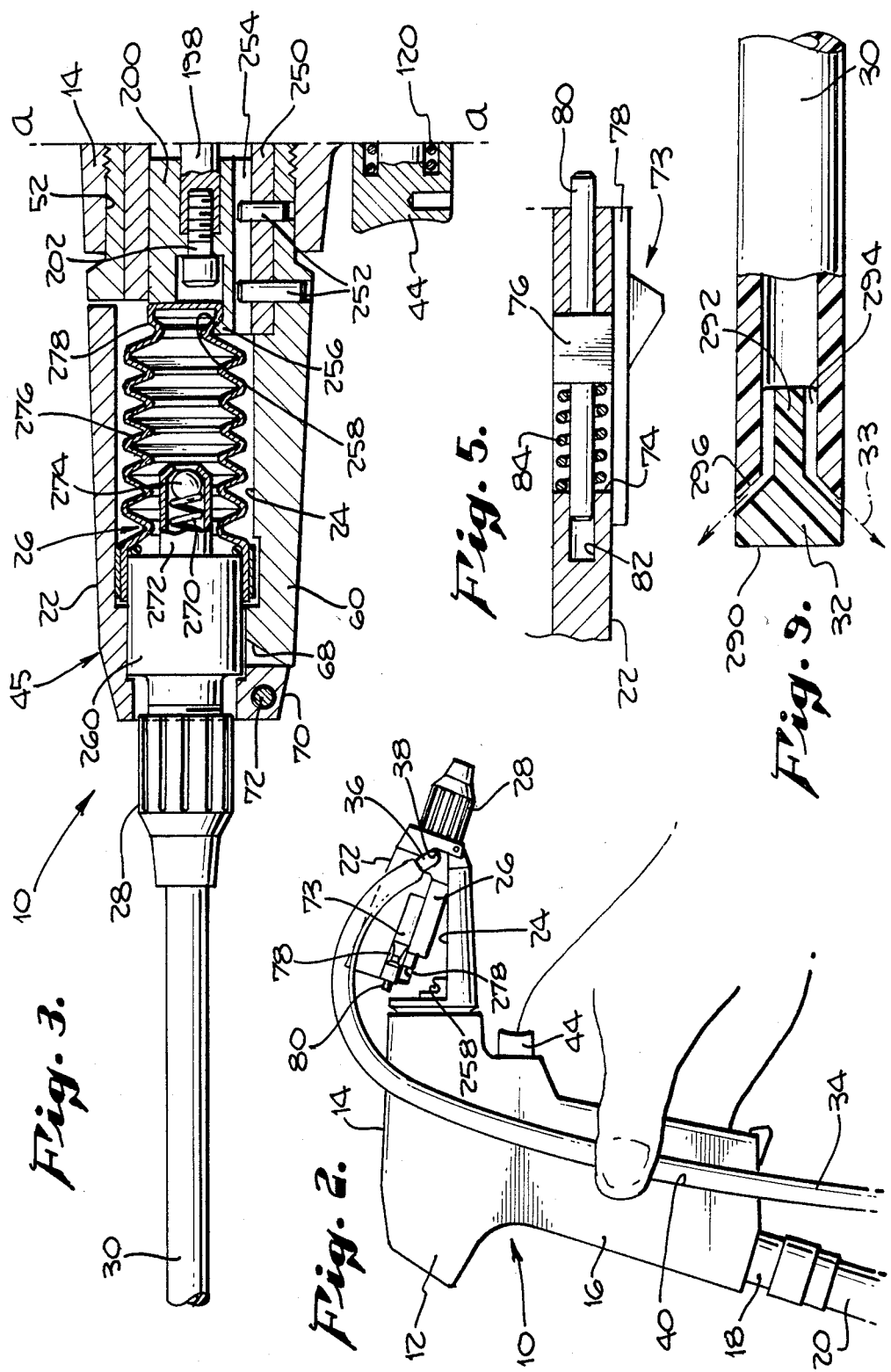

HAND-HELD PULSATING JET LAVAGE

BACKGROUND OF THE INVENTION

1. Field of the Invention

The present invention relates to a hand-held pulsating jet lavage and, more particularly, to an improved jet lavage in which a motor for driving a pulsating fluid pump is mounted within the hand-held housing of the jet lavage and in which the tubing for passing the pulsating fluid is rigid to assure sharp turn-on, cut-off interfaces between the respective pulses.

2. Description of the Prior Art

It is known in the prior art that the use of a pulsating stream of fluid, such as water, can be utilized to cleanse body tissue of contaminates. A well-known example of this is a pulsating device utilized to cleanse the teeth and gums. Such a device is shown in U.S. Pat. No. 3,227,158, issued Jan. 4, 1966, by J. W. Mattingly. This apparatus suffered from a few problems. For one, the motor that provides the energy to pulse the cleansing fluid is mounted within a counter-top container at a substantial distance from the nozzle which delivers the pulsating fluid. When the device is to be used by a surgeon to clean a surgical site, for example, the motor and other major components of the device must be located outside the sterile field surrounding the surgeon and patient. This places the sterile field in jeopardy. A second problem with this apparatus is that there is no adequate arrangement to deliver sterile fluid to the surgical site.

In many devices, the nozzle for fluid delivery is connected to the fluid container by a tube whose flexibility causes a significant deterioration of the turn-on, cut-off interfaces between pulses. See for example, U.S. Pat. No. 3,393,673, which issued July 23, 1968, by J. W. Mattingly; U.S. Pat. No. 3,425,410, which issued Feb. 4, 1969, by M. A. Cammack; and U.S. Pat. No. 3,993,054, which issued Nov. 23, 1976, by G. A. Newman for a therapeutic lavage. The Newman patent relies upon a long and flexible tube to connect its counter-top fluid receptacle to a nozzle. The flexible tube in this device causes the cleansing fluid to be delivered to the body tissue without the sharp interface between pulses originally envisioned.

In the medical profession, many articles have been written noting the advantages of a pulsating jet lavage for the treatment of contaminated wounds. In one paper by Gross, Cutright, and Bhasker, entitled "Effectiveness of Pulsating Water Jet Lavage in Treatment of Contaminated Crushed Wounds," *The American Journal of Surgery*, September 1972, Volume 124, pp. 373-377, the authors' reported on experimentation wherein facial crush wounds were treated with contaminated soil containing bacteria and then lavaged. The control group was irrigated with water using a bulb syringe, while the experimental group was lavaged with a pulsating water jet. The results indicated that the pulsating jet lavage was much more effective in reducing bacterial population and in the removal of necrotic tissue and foreign particles from the wounds than was irrigation with the bulb syringe.

In addition to wound cleansing, the pulsed jet lavage is also useful in total hip replacement surgery. In this application, the pulsed jet lavage is used to remove debris from the intermedullary canal and acetabulum. See the paper by Amstutz, "Femoral Looseness in THR Using Conventional Cement Techniques," *Orthopaedic Review*, May 1980, Vol. IX, No. 5, pp. 33-37.

Yet, another use for pulsating jet lavage is to reduce the trauma caused by the introduction of cement into a bored channel formed within the intermedullary canal of the femoral tip prior to insertion of a prosthesis. It has been found that the introduction of cement into the intermedullary canal causes an increase in blood gas with an accompanying decrease in intrapulmonary shunt fraction and pulmonary artery pressure. By the careful lavage of the plugged intermedullary canal prior to the insertion of the cement, the elimination of gas-exchange and hemodynamic complications can be achieved. See the article by Sherman, Byrick, Kay, Sullivan, and Waddell, entitled "The Role of Lavage in Preventing Hemodynamic and Blood-Gas Changes during Cemented Arthroplasty," *The Journal of Bone and Joint Surgery, Inc.*, April 1983, Volume 65-A, No. 4, pp. 500-505.

SUMMARY OF THE INVENTION

Accordingly, an object of the present invention is to provide the hand-held pulsating jet lavage which is capable of delivering a pulsating fluid to a wound or surgical site in which the pulses have a sharp turn-on, cut-off interface between the pulses.

Another object of the present invention is to provide a pulsating jet lavage that delivers a sterile fluid to the surgical site that is free of contaminants from the hand-held device. A further object is to provide a hand-held jet lavage that delivers a sterile fluid that is isolated from the fluid that drives the hand-held device.

A further object of the present invention is to provide a hand-held pulsating jet lavage in which the hand-held device is separate from a disposable pump cartridge that develops the pulsating jet within the sterile fluid.

Yet another object of the present invention is to provide a pulsating jet lavage in which the hand-held device may be separately sterilized from the disposable pump cartridge which is also capable of sterilization.

In accomplishing these and other objects, there is provided a hand-held housing to which a source of pressurized fluid is applied. The pressurized fluid is controlled by a actuation valve which supplies the pressurized fluid to a pilot valve and then to a motor assembly. The motor assembly drives a reciprocating shaft having a notched end that extends into a chamber within the hand-held housing. The chamber receives a disposable pump cartridge which is retained within a chamber by a chamber closure hatch and has a flanged portion which engages the notch within the reciprocating plunger to assure a positive connection between the reciprocating plunger and the disposable pump. The hand-held housing and its component parts are designed to enable sterilization in high temperature steam. Similarly, the disposable pump cartridge is designed to permit sterilization by irradiation, such as gamma radiation or by ethylene oxide gas.

The invention of the hand-held pulsating jet lavage permits a presterilized pump cartridge to be united with a sterilized housing in the operating room and further permits the insertion of a flexible tube from the pump cartridge into a solution bag for delivering the desired steriled solution from the bag to the pump cartridge. A rigid tube from the pump cartridge to the lavage nozzle assures that the pulses imparted to the sterilized fluid by the pump retain sharp turn-on, cut-off interfaces between the pulsed, nonpulsed portion of the fluid stream.

BRIEF DESCRIPTION OF THE DRAWINGS

Further object and advantages of the present invention will become apparent to those skilled in the art after consideration of the following description and drawings, wherein:

FIG. 1 is a perspective view showing the hand-held pulsating jet lavage of the present invention;

FIG. 2 is a side view showing the hand-held lavage of the present invention with its closure hatch partially open to illustrate the interface of the disposable pump cartridge and the reciprocating plunger;

FIG. 3 is a side elevation of the hand-held pulsating jet lavage broken along line a—a showing the front or left-hand end in a cross-sectional view;

FIG. 5 is a detailed view of the latch which locks the closure hatch into its operating position;

FIG. 8 is a side view, partially in cross section, showing the disposable pump cartridge, flexible tubing, and solution bag spike assembly of the present invention; and FIG. 9 is a detailed cross section of a nozzle useful with the present invention.

DESCRIPTION OF THE PREFERRED EMBODIMENTS

Figure 4:
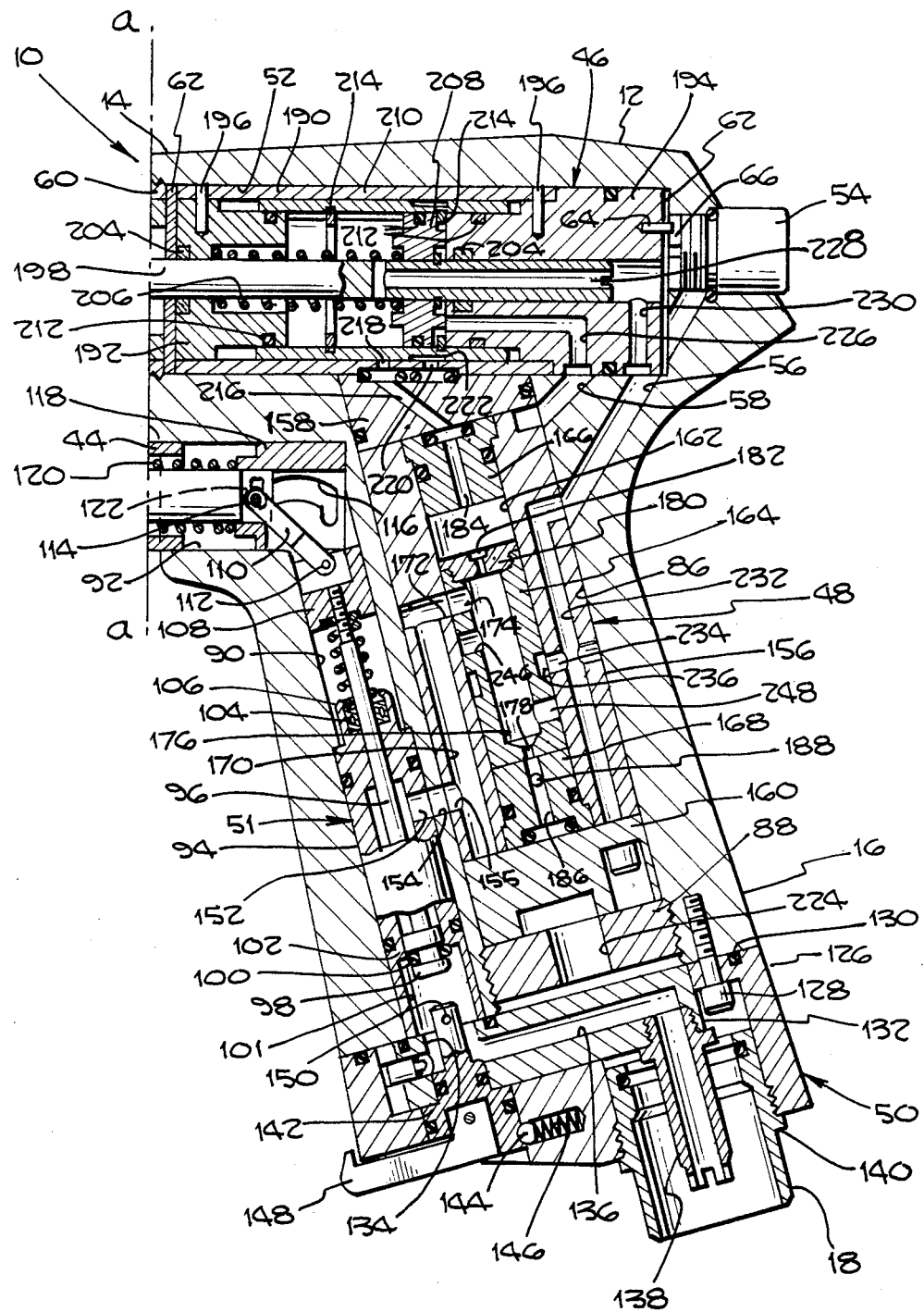
FIG. 4 is a side elevational view of the hand-held pulsating jet lavage broken along line a—a showing the aft or right-hand end in cross section.

Referring now to the drawings, FIG. 1 shows a hand-held pulsating jet lavage 10 having a housing 12 with a pistol-like grip wherein the barrel 14 forms the portion of the housing 12 that is pointed toward the tissue site to be cleansed and a handle 16 is canted back at 15 degrees to a normal to the longitudinal axis of the barrel. The base of handle 16 includes a fluid connection assembly 18 to which is connected via a reinforced flexible hose 20 a source of pressurized fluid, such as compressed air or dry nitrogen, whose pressure may vary between 50 and 160 psi. The front or forward end of the barrel portion 14 of housing 12 includes a hinged hatch cover 22 which, when opened, as seen in FIG. 2, exposes a chamber 24 which receives a disposable pump cartridge 26.

The pump cartridge 26 includes a collar 28 which extends from the barrel 14 and removably mounts a rigid tubing 30 whose unsupported end terminates at a nozzle 32. Sterilized fluid 33 is supplied to the pump cartridge 26 by a flexible tubing 34. The flexible tubing is connected at one end to an elbow 36, FIG. 2, which passes through aperture 38 within the hatch 22. Thereafter, the flexible tubing is curved to a convenient arc so that it will not kink and inserted into a groove 40 within the handle 16. Groove 40 prevents the flexible tubing from interfering with the user during operation of the pulsating jet lavage 10. The housing 12 and its internal moving components are constructed from noncorrosive, highly polished materials which operate free of any liquid lubricants.

The disposable pump cartridge 36 and its flexible tubing 34 which is terminated by a bag spike 42 and protective cover 43, FIG. 8, are constructed from material such as polypropylene, polyethylene or clear acrylic. The disposable pump cartridge and its components are assembled, placed within a sealed bag and sterilized by irradiation, such as gamma rays. Ethylene oxide gas can also be used. Similarly, housing 12 and its components may be sterilized by placement in an autoclave and exposure to steam at 275° F., 30 psi, for 45 minutes, for example. Through the present invention, it is possible to quickly and fully sterilize the hand-held housing 12 and the disposable pump cartridge 36.

In operation, the user of the pulsating jet lavage takes up a sterilized housing 12, opens the hatch 22 and inserts a sterilized pump cartridge assembly 26. Thereafter, the hatch 22 is closed, the flexible tubing 34 is inserted into groove 40, the bag spike 42 is inserted into a solution bag, not shown, and the air hose 20 is connected to hose connection assembly 18. In this configuration, the hand-held pulsating jet lavage 10 is ready for operation fully within a sterile field surrounding the surgeon and patient. Operation is accomplished by simply depressing the trigger 44 and pointing the nozzle 32 at the surgical site the user wishes to cleanse.

Referring now to FIGS. 3 and 4 which are a cross section of housing 12 separated along line a—a, it will be seen that the pulsating jet lavage 10 incorporates several subassemblies including: the chamber closing assembly 45 including hatch 22 (FIG. 3), a motor assembly 46 (FIG. 4), a pilot valve assembly 48 (FIG. 4), handle closure assembly 50 (FIG. 4) and the actuation slider assembly 51 which includes trigger 44 (FIG. 4).

Housing 12 is formed from an aluminum alloy and bored along its barrel portion at 52 to receive the motor assembly 46. The bottom of bore 52 is open with a threaded opening which receives a threaded plug 54. The plug 54 closes an opening through which the appropriate tools are inserted to bore passageways 56 and 58. The opening of the bored aperture 52 is threaded to receive a tubularly shaped pump cradle 60 whose threaded portion retain the motor assembly 46 in the desired longitudinal position with the assistance of shims 62 which may be inserted at the bottom of the bore 52 and at the top of the bore 52 between the motor assembly 46 and pump cradle 60. A pin 64 inserted into the aft-end of the motor assembly 46 fits within a slot 66 in the bottom of plug 54 to further locate assembly 46.

The pump cradle 60 includes a tubular aft portion or right-hand portion as viewed in FIG. 3 and partially in FIG. 4, which has been threaded for mounting within the housing 12 as stated above. The forward portion is relieved to form a semicircular cradle which receives the pump cartridge 26. The forward or left-hand most end of the cradle 60 is slotted at 68 to receive a tab 70 extending from hatch 22 which is retained therein by a pin 72.

As best seen in FIG. 5, the chamber closure assembly 45 includes a pair of latch assemblies 73 mounted in a pair of rectangular openings 74 on opposite sides of hatch 22. Each assembly 73 includes a shoulder 76 extending from a slider 78 into opening 74. The shoulder 76 is bored to receive a latch pin 80 which extends into a bored opening 82 beyond the rectangular opening 74. Pin 80 is retained within the shoulder 76 as by force fit but slides freely within the bored opening 82. A spring 84 completes the latch assembly 73. It should be noted that there are two latch assemblies 73 function independently from one another. Thus, there is an added safety feature in that one or both of the latch assemblies 73 should latch the hatch 22 in the closed position for retaining the pump cartridge 26 within the chamber 24 formed between pump cradle 60 and hatch 22.

The handle 16 of housing 12 is also opened with a bore 86 which extends from the base of the handle to intersect bore 52 at an angle of 15° to a perpendicular to the longitudinal axis of bore 52. The opening portion of bore 86 is threaded to receive a plug 88 which forces the pilot valve assembly 48 into a tight fitting arrangement with motor assembly 46. Parallel to the bore 86 is a second smaller bore 90 which passes from that lower portion of handle 16 to a trigger receiving bore 92 which is bored parallel to the motor mounting bore 52. The trigger assembly 51 is assembled by inserting a tubularly shaped distributor 94 into the bore 90. The distributor 94 is bored through to receive a poppet valve stem 96 whose lower end mounts a grooved collar 98 which in turn mounts an O-ring 100. The lower portion of distributor 94 is counterbored to form a chamber 101 and a shoulder 102 against which the O-ring 100 rests. Poppet valve stem 96 extends beyond the distributor 94 through a seal 104 which is retained within the distributor by a cap 106. The upper end of valve stem 96 is threaded for mounting within a tappet 108 which slidably mounts within the bore 90. Tappet 108 is connected to the trigger 44 by a link 110 whose lower portion fits within a slot in the tappet 108 and is retained therein by a pin 112. The upper portion of link 110 is bifurcated to surround a flat portion on trigger 44 and is retained therein by a pin 114. Pin 114 is long enough to extend into a pair of cam grooves 116 of a cam bushing 118 which is mounted in the bottom of the trigger bore 92. Trigger 44 is surrounded by a spring 120 which rides against the cam bushing 118 for urging the trigger 44 into its outwardly extended position.

Depression of trigger 44 causes a pair of rollers 122 mounted on the outer ends of pin 114 to move to the right, FIG. 4, and to roll within the cam grooves 116. It will be seen that the initial displacement of trigger 44 causes the link 110 to pivot about pin 112 and to move in nearly a circular motion for displacing tappet 108 only slightly. As the angles of the cam groove 116 change, further displacement of trigger 44 forces the pin 114 to follow a tighter radial path for forcing link 110 down further, thus moving tappet 108 in a downwardly direction for further opening the closure formed by O-ring 100 against shoulder 102. The cam grooves 116 thus produce an initially high mechanical advantage for a small trigger displacement that overcomes air pressure applied through connector 18 to the chamber 101 formed in the lower portion of distributor 94 which can vary between 50 and 160 psi.

Pressurized air or nitrogen is supplied to chamber 101 through the handle closure assembly 50 which includes a shoe 126 mounted to the handle 16, as by screws 128. The shoe 126 is sealed against the lower surface of handle 16 by an O-ring 130. The reader should note that O-rings are extensively used throughout the assembly of the hand-held pulsating jet lavage. For brevity each O-ring will not be separately described. Shoe 126 includes a chamber which receives a connector mounting block 132 having a first aperture 134 which communicates with chamber 101. A lateral aperture 136 joins a third aperture which parallels the chamber 134 and which is threaded to receive an inner inlet connector 138. An outer inlet connector 140 is coaxially threaded into the shoe 126 about connector 138 to form the hose connector assembly 18. The first aperture 134 extends through the shoe 126 to receive a coupling plug 142 which is sealed within the shoe 126 and block 132 by O-rings. The coupling plug 142 is retained in its preferred position by a detent 144 that is urged by a spring 146 against the outer periphery of the plug 142. A turning key 148 mounts within keyway in plug 142 to transfer a rotational force to the plug. A pin 150 passes through the upper stem of plug 142 and fits within a slot, not shown, in the base of distributor 94. It will be seen that the routine of key 148 rotates the plug 142 which, in turn, rotates distributor 94 within the bored opening 90. The inner bore of distributor 94 is provided with a lateral aperture 152 which is shown in communication with a port 154 to join the bore 90 which receives distributor 94 with the bore 86 which receives the pilot valve assembly 48.

Pilot valve assembly 48 is provided with a pressure inlet port 155 to communicate with the ports 152 and 154 under normal conditions. Rotation of key 148 causes the rotation of distributor 94 and the misalignment of lateral aperture 152 with the pressure inlet ports 154 and 155. Thus, it will be seen that the key 148 can act as a safety switch to terminate the flow of pressurized air through the inner connector 138, lateral aperture 136, chamber 134, chamber 101, around shoulder 102 and through the aperture 152 to the port 154 and port 155 of the pilot valve assembly 48. Key 148 may also be used to partially close aperture 152 from port 154 for lowering the air flow and operating pressure delivered to the pilot valve assembly 48 and motor assembly 46. At a lowered pressure and flow rate, the trigger 44 can control the speed of the motor assembly from 0 to 1800 cycles per minute, for example. At higher pressures, above 50 psi, for example, the hand-held lavage tends to lock onto a desired frequency. Below 50 psi the rules of operation change and the pilot valve 48 no longer controls the movements of the motor 46. Thus, the hand-held lavage of the present invention is capable of delivering a sterile pulsed fluid with an adjustable pulse rate at low pressure.

Pilot valve assembly 48 includes a housing 156 which slidably fits within bore 48. The upper end of housing 156 is closed by a manifold end plate 158 sealed within the bore 86 by O-rings, while the lower end of housing 156 is closed by an exhaust manifold 160. Housing 156 is provided with a longitudinal bore 162 which receives a poppet 164 and and which is closed at its upper and lower ends by an upper plug 166 and a lower plug 168.

In FIG. 4, only two of the five pressure or exhaust channels are shown in housing 156. A first pressure input channel 170 communicates with port 155 and passes up the left-hand side of housing 156. A lateral port 172 communicates from port 170 into the longitudinal bore 162 of housing 156 and is aligned with an input port 174 within the poppet 164. Input port 174 opens into a poppet chamber 176 which is longitudinally drilled within the poppet 164 and opened at its lower end by a small bleeder port 178. The upper end of the poppet chamber 176 is closed by a threaded button 180 having a longitudinal bleeder port 182 therein. It will be seen that the poppet 164 is free to slide within bore 162 between the upper and lower plugs 166 and 168, respectively. Plug 166 has a central passageway 184 which communicates to the manifold end plate 158. Similarly, plug 168 has a pair of passageways, a longitudinal passageway 186 and a lateral passageway 188. It will be seen that pressure passing up the input channel 170 passes through ports 172 and 174 into the poppet chamber 176 where the pressure is bled through the lower and upper bleeder ports 178 and 182, respectively. Pressure from bleeder port 178 is passed through the plug passageway 184 and the manifold end plate 158 to the motor assembly 46. Similarly, the pressure through lower bleeder port 178 passes down the passageway 186, through the lateral passageway way 188 and up a passageway, not shown, in housing 156 to pass through the manifold end plate 158 to the motor assembly 46. The remaining functions of the pilot valve assembly 58 will be described hereinbelow with regard to FIGS. 6 and 7 when the operation of the pulsating jet lavage 10 is described.

The motor assembly 46 comprises a cylinder 190 whose forward or left-hand end is plugged with a forward plug 192 and whose aft or right-hand end is plugged by an aft plug 194. Plugs 192 and 194 are retained and oriented in cylinder 190 by pins 196. It will now be seen that pin 64 extends from the aft ends of plug 194 to locate the motor assembly 48 in slot 66 of plug 54. The plugs 192 and 194 have been longitudinally bored to receive a piston rod 198 which extends beyond the forward plus 192 to mount a reciprocating plunger 200, FIG. 3, which extends into the chamber 24 and is retained on the end of rod 198 by a screw 202. The piston rod 198 is sealed within plugs 192 and 194, FIG. 4, by seals 204 and is spring-loaded by a spring 206 to normally urge the piston rod 198 toward the aft portion of motor assembly 48. The spring 206 is seated between the forward plug 192 and a piston 208.

It will be seen that the piston 208 slides in a reciprocal motion within a timing sleeve 210 which, in turn, slides on the outer portions of the forward and aft plugs 192 and 194 between the plugs and the inner surface of cylinder 190. The cylinder 190 is manufactured from corrosion resistant steel and polished along its inner surface to a smooth finish. The forward and aft plugs 192 and 194 and the timing sleeve 210 are manufactured from bronze that is highly polished. The piston rod 198 is manufactured from corrosion resistant steel, while the piston 208 is manufactured from an aluminum alloy. The piston 208 and foward and aft plugs, 192 and 194, are each provided with a piston ring 212 manufactured from teflon impregnated with graphite. A pair of snap rings 214 are inserted into the inner diameter of timing sleeve 210 to engage the piston 208 as it moves back and forth within the motor assembly 46.

In the position shown in FIG. 4, pressure from the chamber formed by the bore 162 passes through the passageway 184 in plug 166 and then through a manifold passageway 216 to pass through an aperture 218 in motor cylinder 190. In the position shown the pressure in passageway 184 is retained by the position of the timing sleeve 210 which blocks aperture 218 from an exhaust port in manifold 158, not shown. In a similar manner, pressure from poppet chamber 176 which passed through bleeder 178 and passageways 186 and 188, has been directed through a passageway, not shown, within housing 156 to a second aperture 220 in motor cylinder 190 where it passes into an annular groove 222 within the timing sleeve 210 and then to an exhaust port, not shown, which communicates with the annular groove 222 and passes through the manifold end plate 158, housing 156, exhaust manifold 160, to pass through an aperture 224 within plug 88 and then around block 132 and out between the innerconnector 138 and outer hosing connector 140. It will be understood that the low pressure on the downward side of poppet 164, when contrasted with the pressure within upper chamber 162, will retain the poppet 164 in the position shown.

Similarly. pressure from poppet chamber 176 passes out of the poppet, in the position shown in FIG. 4, through an aperture, not shown, which communicates with a passageway through housing 156 to the upper end of that housing where the pressure is passed into passageway 58 which communicates with a passageway 226 in aft plug 194. This provides pressure to the right-hand side of piston 208 for forcing the piston to move to the left, FIG. 4. As the piston moves to the left, the piston chamber shown to the left of piston 208 in FIG. 4 is exhausted through a central passageway in 228 in piston rod 198. This passageway exhausts into the central bore of aft plug 194, through a vertical passageway 230 in plug 194 to communicate with passageway 56 located in housing 12. Passageway 56 exhausts it pressure through a longitudinal passage 232 in housing 156 closed at its lower end by the exhaust manifold 160 but provided with a lateral passageway 234 which communicates with an annular groove 236 in poppet 164. The exhaust pressure within the annular groove 236 is then exhausted through a slot, not shown, in housing 156 which communicates to the exhaust manifold 160 and then to the connector 18.

Figure 6:
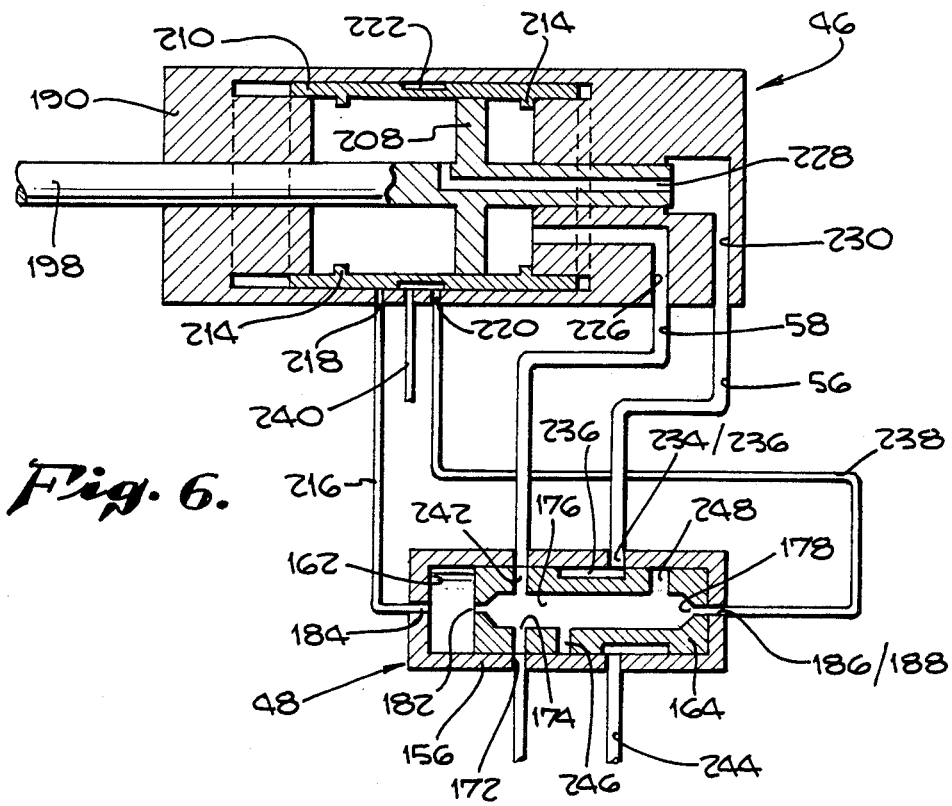
FIG. 6 is a schematic diagram illustrating the operation of the hand-held pulsating jet lavage motor and pilot valve.

Referring now to FIG. 6, the operation of the pilot valve assembly 48 and motor assembly 46 is shown. Note that the position of piston 208 in FIG. 6 is slightly to the left from the piston position shown in FIG. 4. Also note that all components identified above have been numbered with the corresponding numbers in FIGS. 6 and 7. If the reader were to draw a horizontal line between the pilot valve assembly 48 and motor assembly 46, he would note there are five channels joining the two assemblies. These five channels pass through the housing 156 and communicate either through the manifold end plate 158 or the housing 12 to the motor assembly 48. Three of these passageways are shown in FIG. 4 within the housing assembly 156 while one passageway is shown in the manifold end plate 158 and two passageways are shown in housing 12. Thus, the reader will realize that two passageways in housing 156 are not shown but are obscure from view in FIG. 4 while two passageways in manifold 158 are also obscure.

Referring to FIG. 6 and recalling the explanation given thus far, the reader will understand that pressure has been delivered through port 172 and input port 174 to the poppet chamber 176. This pressure is permitted to escape in the configuration shown through three of the several outlets including bleeder ports 178 and 182. The pressure communicated from bleeder port 182 along line 216 is prevented from escaping by the position of the timing sleeve 214 blocking aperture 218. However, pressure from poppet chamber 176 passes through the passageways 186 and 188 into a line 238, not shown in FIG. 4 in housing 156 and manifold end plate 158, to enter aperture 220 in cylinder 190 where it travels through the annular groove 222 in timing cylinder 214 to be exhausted from exhaust line 240 shown only in FIGS. 6 and 7.

The third opened port from poppet chamber 176 is an output port 242, not shown in FIG. 4, which communicates with passageway 58 and the piston cylinder formed on the right-hand side of piston 208. The reader will now understand that pressure on the right-hand surface of piston 208 will force that piston and its piston rod 198 to move toward the left-hand side of FIG. 6. As the piston does so, the air in the chamber to the left of piston 208 is exhausted through the central passageway 228 within piston rod 198, through the vertical passageway 230, and the passageway 56 in the handle of housing 12. The exhaust pressure is then passed down the longitudinal passageway 232 within pilot valve housing 156 and through the lateral passageway 234 into the annular groove 236 in poppet 164. From here the pressure circumvents the poppet to be exhausted through an exhaust port 244, shown only in FIGS. 6 and 7. Exhaust port 244 terminates in the lower portion of pilot valve assembly 48 to permit the escape of exhaust pressure through the aperture 224 in plug 88 and thence between the connectors 138 and 140 of the hose connection assembly 18.

Figure 7:
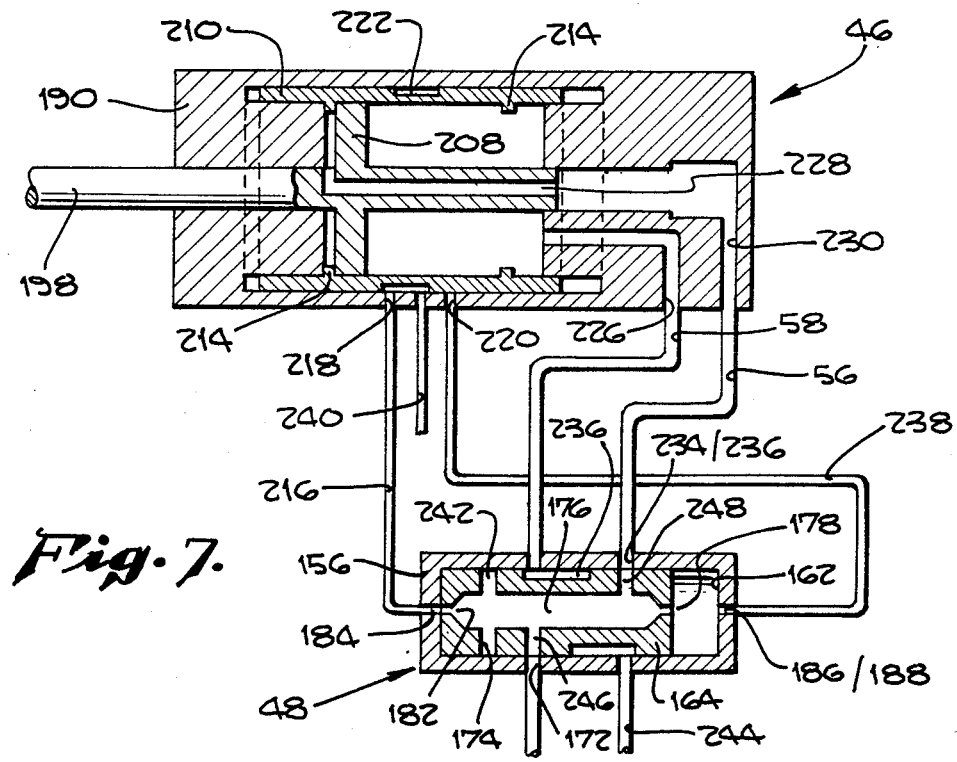
FIG. 7 is a schematic diagram, similar to FIG. 6, illustrating the operation of the hand-held pulsating jet lavage.

As piston 208 moves toward the left in FIG. 6, the outer edge of the piston strikes the left most snap ring 214 for moving the timing sleeve 210 to the left, as shown in FIG. 7.

Once timing sleeve 210 has been moved to the left, it will be seen that the pressure in port 218 which was retained by the timing sleeve is now exhausted around the annular groove 222 within sleeve 210 and out through exhaust line 240. Conversely, the line 238 which had its pressure, passing through aperture 220, exhausted through the line 240 is now closed by the timing sleeve 210. Thus, pressure begins to build within the poppet receiving bore 162 on the right-hand surface of poppet 164, FIG. 7. The pressure that had been retained in that same chamber on the left-hand side of the poppet 164 is now exhausted to the atmosphere. Thus, the poppet 164 will slide to the left, FIGS. 6 and 7, within its housing 156 which closes the pressure outport port 242.

However, a second pressure input port 246 in poppet 164 is now in alignment with the port 172 in housing 156. The previously aligned port 174 is now sealed by the inner surface of housing 156. Similarly, a second output port 248 has moved from its sealed position in FIG. 6 to an open position in FIG. 7 where it is aligned with the lateral passageway 234 and longitudinal passageway 232. In the same motion, the annular groove 236 in the poppet 164 has moved from alignment with the lateral passageway 234 to align itself with passageway 58 which was previously aligned with output port 242. With the poppet 164 in the position shown in FIG. 7, pressure now begins to build on the left-hand surface of the piston 208 through the second output port 248, lateral passageway 234, passageway 56, vertical passageway 230, and central passageway 228 in piston rod 198. As the rod begins to move to the right, FIG. 7, the chamber formed to its right is exhausted through the passageway 226, passageway 58, and annular groove 236 in poppet 164 to eventually exhaust between the connectors 138 and 140. The reader will now understand that under full pressure the piston rod 198 is driven back and forth in a reciprocal motion by the flow of pressurized air through the pilot valve assembly 48 and motor assembly 46.

Depression of trigger 44 opens the poppet valve formed by O-ring 100 against shoulder 102 for controlling the flow of air into the pilot valve assembly 48. The present invention is thus capable of throttle control of the motor assembly from 0 to 2500 cycles per minute. In a preferred configuration, the motor locks at a desired frequency, for example, 1800 cycles per minute, and retains that frequency in spite of variations in pressure above approximately 50 psi. It will be seen that the rotation of key 148 which rotates the distributor cylinder 94 to misalign the lateral aperture 152 from the pressure input port 154 may be used as a safety on selector switch. However, below 50 psi, for example, the pulsed jet lavage operates at a variable speed device. This lower pressure may be obtained by the partial closure of aperture 152 from port 154.

Referring to FIGS. 3 and 8, the details of the preferred embodiments of the pump cartridge 26 are shown. First, the reader should note that plunger 200 reciprocates within a bushing 250 made from a low friction, high wear material such as DuPont's Vaspel 211. The plunger 200 is retained in its desired position by a pair of pins 252 which pass through the pump cradle 60 and extend beyond the innerdiameter of bushing 250 to ride within a groove 254 within the plunger 200. A semicircular lip 256 extends from the lower, left-hand surface of plunger 200 having an upwardly extending member which forms a notch 258. Notch 258 is most important as it positively engages the disposable pump cartridge 26 to assure a positive transmittal of forward and backward motion to the pump 26 by the motor 46.

The disposable pump cartridge 26 will be seen to incorporate two embodiments. The pump cartridge 26 includes a body member 260, FIG. 8, which has been drilled through along its longitudinal axis and then bored from opposite ends to form a mid-shoulder 262. The outward bore of member 260 receives the rigid tubing 30 which bottoms against shoulder 262 when inserted into the body member 260. By rotating the collar 28 upon its threaded connection to body member 260, an O-ring 264 is compressed against the rigid tubing 30 for retaining that tubing in its desired position. On the opposite side from tubing 30, the body member 260 has been formed with a toroidally shaped chamber 266 concentric to the bore with an outer surface opened by an aperture 268 that communicates through elbow 36 to form a fluid path for the sterilized fluid within tubing 34. A spring 270 is inserted into the bore of body member 260 to rest against the inner surface of shoulder 262 and is retained therein by a tubular cap member 272 whose outer end is partially closed to retain a ball valve 274 which is urged against the partial closure by the action of the spring 270.

The outer surface of body member 260 beyond the toroidal chamber 266 is closed in one embodiment by a bellows 276, FIG. 3, whose outer end is provided with a flange 278 that engages the notch 258 for positively connecting the bellows 276 to plunger 200. In the embodiment shown in FIG. 3, the molded bellows 276 has a natural spring action that urges the bellows into the extended position shown.

Referring again to FIG. 8, it will be seen that the bellows 276 is replaced with a cylinder 280 in a second embodiment of the pump 26. The outer most end of cylinder 280 has an inwardly directed shoulder 282 and its inner most end mounts over and encloses the outer surface of body member 260. The shoulder 282 retains a piston 284 which is sealed within the cylinder 280 by an O-ring 286 and which is urged against the flange 282 by a spring 288. It will be noted that the piston 284 also incorporates the flange 278 for positive engagement with the notch 258 of bushing 200. A diaphragm ring 289 is inserted between cylinder 280 and body member 260 to complete the pump assembly 26.

The reader should note that the pump cartridge 26 is spring-loaded to be returned to the extended position shown in FIGS. 3 or 8. Similarly, the motor assembly 46 is spring-loaded by spring 206 to return the piston rod 198 to its retracted position as shown in FIGS. 3 and 4. In this configuration, the pump 26 automatic aligns itself with the plunger 200 of motor assembly 46 when the pump cartridge 26 is inserted into the chamber 24. Once in the position shown in FIG. 2, the hatch 22 may be easily closed to retain the pump 26 in the desired position with its flange 278 securely engaged into the shoulder formed by notch 258.

Referring now to FIG. 9, the rigid tube 30 is shown with a unique and simple nozzle 32 which is formed by simply chamfering the end of rigid tube 30 at an inwardly directed angle of 45° and inserting a plug 290 that has been reduced to form an extended pin portion 292 which fits within the internal diameter of tube 30. Eight grooves 294 are then cut along the outer surface of the extended pin 292 and up the side walls of a 45° shoulder 296 formed within the plug 290. These grooves conduct a spray of water at an angle of 45° from the tip of the nozzle 32. This spray works more efficiently at 45° than prior art sprays which were directed at 90° to the axis of the nozzle or parallel thereto. Further, the low profile of nozzle 32, being no larger than the outer diameter of tube 30 is convenient for insertion within bored channel in the intermedullary canal of the femur.

The hand-held pulsating jet lavage thus described delivers a stream of sterile irrigation fluid to a surgical site with a pulse that has a sharp interface. The present invention permits the pulsating jet lavage to be turned on slowly and then brought up to speed quickly with a unique trigger actuated valve arrangement 51. Further, the pilot valve assembly 48 and motor assembly 46 is designed to provide a reliable power source for the separate pump cartridge 26. The reader will understand that the poppet 164 controls the frequency of the motor assembly 46. That is, the poppet bleeder ports 178 and 182 from poppet 164 control the escape of pressure from chamber 176 which, in turn, control the frequency of the motor assembly 46. In the present embodiment, it will be noted that the passageway from bleeder port 178 to the motor assembly 46 is longer than the passageway from bleeder port 182 to the motor assembly. To adjust for this, the bleeder port 182 has been machined to a slightly smaller diameter than bleeder port 178. In the preferred embodiment, bleeder port 182 is 0.015±0.0005 inches while bleeder port 178 is 0.016±0.0005 inches. While other dimensions and tolerances are clearly possible, the reader will understand that the unique pilot valve assembly 48 may be easily adjusted during manufacture to accommodate for different frequencies by simply adjusting the size of bleeder ports 178 and 182.

While the spring-loaded cartridge 26 and spring-loaded motor assembly 46 are returned to their ready position, the reader will note that motion of piston 208 moves timing sleeve 210 to its start position and generates a pressure within the poppet chamber 162 to urge the poppet into the position shown in FIG. 4. Further, gravity will urge the poppet into the position shown when the user picks up the hand-held lavage 10 to commence operation. Thus, the pilot valve 48 and motor assemblies 46 are always in a ready position for easy starting as trigger 44 is depressed. After having reviewed the foregoing, the reader will understand how it is possible to fully sterilize the hand-held housing 12 in a steam autoclave while sterilizing the disposable pump cartridge and its components in a sealed transparent bag utilizing gamma rays. It will also be understood how the two components may be simply joined by opening the sealing bag, removing the sterilized pump chamber 26, and then opening hatch 22 by sliding the latch assembly 73 to remove pins 80 from pump cradle 60. As the hatch 22 pivots into an open position around pin 72, the pump cartridge 26 may be easily inserted into chamber 24 with pump flange 278 easily engaging plunger notch 258. Thereafter, the hatch 22 is closed for locking pump 26 into permanent engagement with motor assembly 46 through the interaction of the flange 278 with notch 258. The user then inserts flexible tubing 34 into groove 40 to permit ease of operation. The collar 28 is then loosened, the appropriate nozzle tube 30 inserted, and the collar tightened again. The cover 43 is removed from bag spike 42 which is then inserted into a bag of sterile solution, not shown, and the air hose 20 is connected to hose connection assembly 18. Thereafter, the safety switch 148 is moved to the on position and the hand-held pulsating jet lavage is ready to operate.

What is claimed is:

1. A hand-held pulsating jet lavage driven by a source of pressurized fluid for delivering discrete fluid, pulses with sharp turn on and cut off interfaces, (to deliver a pulsed fluid) from a second source, comprising:

hand-held housing means for receiving said pressurized fluid from said second source;

motor means mounted within said hand-held housing means driven by said pressurized fluid;

said hand-held housing having a chamber therein;

reciprocating means driven by said motor means, the reciprocating means extending into said chamber for reciprocation along a selected axis;

disposable pump cartridge means connected to said second source;

said chamber having closure means, the opening of which permits reception of said disposable pump cartridge means; and means for engaging said disposable pump cartridge means and said reciprocating means for moving the pulsed fluid generally parallel to the selected axis in response to reciprocation of the reciprocating means, whereby said fluid from said second source is isolated from said hand-held housing means and said pressurized fluid.

2. A hand-held pulsating jet lavage, as claimed in claim 1, wherein:

said reciprocating means includes plunger means connected to said motor means having a notched end extending into said chamber; and said disposable pump cartridge means includes a flange which fits within said notched end and is positively retained therein by closure of said closure means.

3. A hand-held pulsating jet lavage, as claimed in claim 1, wherein:

said motor means includes means for urging said motor meanas and said reciprocating means into a predetermined position; and said disposable pump cartridge means includes means for urging said pump means into a predetermined position, whereby said reciprocating means and said pump means are automatically aligned for reception of said pump means into said chamber.

4. A hand-held pulsating jet lavage, as claimed in claim 1, wherein:

said disposable pump cartridge means includes flexible tubing means for connection to said second source of fluid; and said hand-held housing means includes a groove to receive said flexible tubing means.

5. A hand-held pulsating jet lavage, as claimed in claim 1, wherein:

said disposable pump cartridge means includes a nozzle and rigid nozzle tube wherein said motor means drives said pump means through said reciprocating means to pulse said fluid from said second source through said rigid nozzle tube and said nozzle with a sharp turn on, cut off interface between said pulses.

6. A hand-held pulsating jet lavage for delivery of a fluid from a source of fluid, comprising:

a hand-held housing having a chamber therein;

a reciprocating plunger mounted within said housing extending into said chamber;

means for driving said plunger in a reciprocating motion along a selected axis;

a disposable pump removably mounted within said chamber in positive engagement with said plunger; and means for connecting said source of fluid to said disposable pump wherein said fluid moves generally parallel to the selected axis in response to reciprocation of the plunger.

7. A hand-held pulsating jet lavage, as claimed in claim 6, wherein:

said fluid is sterile fluid.

8. A hand-held pulsating jet lavage, as claimed in claim 7, wherein said dispoable pump includes:

collar means threadably mounted upon said pump;

nozzle means passing through said collar means; and sealing means mounted between said collar means and said pump wherein tightening of said threadably mounted collar means urges said sealing means against said nozzle means.

9. A hand-held pulsating jet lavage, as claimed in claim 8, wherein:

said nozzle means includes a rigid nozzle tube wherein said sterile fluid is driven into a pulsated stream having a sharp interface between pulses.

10. A hand-held pulsating jet lavage, as claimed in claim 6, wherein:

said reciprocating plunger has a notched end; and said disposable pump has a flanged end portion that positively engages said notched end of said plunger.

11. A hand-held pulsating jet lavage, as claimed in claim 6, wherein:

said chamber includes a closure hatch;

said plunger has a notched end extending into said chamber;

said disposable pump has a flanged portion which engages said plunger notch; and said closure hatch automatically retains said pump in engagement with said plunger upon closure thereof.

12. A hand-held pulsating jet lavage, as claimed in claim 6, wherein said means for driving said plunger include;

a source of pressurized fluid;

a pilot valve assembly; and a motor assembly driven by said pressurized fluid under the control of said pilot valve assembly.

13. A hand-held pulsating jet lavage, as claimed in claim 12, wherein said motor assembly includes:

a housing cylinder;

forward and aft plugs closing said housing cylinder;

a piston rod slidably mounted within said plugs;

a piston mounted upon said piston rod; and a timing sleeve slidably mounted upon said forward and aft plugs between said piston and said housing cylinder.

14. A hand-held pulsating jet lavage, as claimed in claim 13, additionally comprising:

internal stop means mounted upon said timing sleeve on opposite sides of said piston which engage said piston only after said piston has travelled a predetermined length to deliver relatively high power at a relatively slow speed to said piston rod.

15. A hand-held pulsating jet lavage, as claimed in claim 12, wherein said pilot valve assembly includes:

a housing which receives said pressurized fluid;

poppet means slidably mounted within said housing having an inner chamber;

said housing having a pressure port and an exhaust port;

said poppet means having at least one aperture that communicates between said inner chamber and said pressure port to apply pressure to said inner chamber;

said poppet means further having a pair of control bleeder ports which direct said pressurized fluid to said motor assembly to control the frequency of said motor assembly.

16. A hand-held pulsating jet lavage, as claimed in claim 15, wherein;

said pair of control bleeder ports may be adjusted to adjust in size to adjust the frequency of said motor.

17. A hand-held pulsating jet lavage, as claimed in claim 6 additionally comprising:

a source of pressurized fluid connected to said housing;

control valve means for controlling the flow of said fluid mounted within said housing;

actuation slider means connected to said control valve means for opening said control means.

18. A hand-held pulsating jet lavage, as claimed in claim 17, wherein said actuation slider means includes:

a trigger-like actuator mounted within said housing; and cam means joining said trigger-like actuator to said control valve means for opening said valve means by an amount less than the displacement of said trigger-like actuator.

19. A hand-held pulsating jet lavage, as claimed in claim 17, wherein said control valve means includes:

said housing having a cylindrically shaped aperture for receiving said control valve means;

a cylindrically shaped housing rotatably mounted within said cylindrical aperture;

a poppet shaft connected to said actuation slider means passing through said cylindrically shaped housing;

said hand-held housing having an aperture therein for passing said pressurized fluid from said control valve means;

said cylindrically shaped housing having an aperture therein in nominal alignment with said last mentioned aperture within said hand-held housing aperture; and means for rotating said cylindrically shaped housing to remove said nominal alignment between said cylindrically shaped housing aperture and said hand-held housing aperture to regulate the flow of said pressurized fluid, wherein said actuation slider means controls the pulse rate of said pulsated stream.

20. A hand-held pulsating jet lavage, as claimed in claim 6, wherein:
said hand-held housing and its components are construed of polished and smooth, oil free moving components that may be sterilized by high pressure steam; and
said disposable pump is constructed of material that may be sterilized by irradiation.

21. A hand-held pulsating jet lavage, as claimed in claim 20, wherein:
said irradiation is gamma radiation.

22. A hand-held pulsating jet lavage, as claimed in claim 6, wherein said disposable pump includes:
a tubular pump body member having a threaded outer end;
a collar mounted upon said threaded outer end;
a rigid nozzle tube inserted through said collar and against said tubular pump body member; and
sealing means mounted about said rigid nozzle tube and between said collar and said body member for compression upon said tube as said collar turns upon said threaded outer end.

23. A hand-held pulsating jet lavage, as claimed in claim 22, wherein said rigid nozzle tube includes:
said rigid tube having an outer end terminated with a chamfer;
a plug inserted into said chamfered end of said tube;
said plug having a shoulder with a sloped surface matching said chamfered end and
grooves extending along said plug and across said sloped surface to permit the escape of said fluid at an angle equal to the angle of said chamfered end.

24. A hand-held pulsating jet lavage, as claimed in claim 6, wherein said disposable pump includes:
a tubular pump body member having a toroidally shaped chamber;
sterile means for introducing said fluid into said chamber;
expandable means for expanding and contracting said chamber; and
said expandable means having a flange which positively engages said reciprocating plunger.

25. A hand-held pulsating jet lavage, as claimed in claim 24, wherein said expandable means includes:
a bellows having pleated members which urge said bellows into an expanded position.

26. A hand-held pulsating jet lavage, as claimed in claim 24, wherein said expandable means includes:
a cylinder mounted about said chamber;
piston means slidably mounted within said cylinder to close said chamber; and
spring means to urge said piston into an expanded position.

27. A hand-held pulsating jet lavage, as claimed in claim 24, wherein said disposable pump further includes:
means for closing said chamber during said expansion thereof; and
means for closing said chamber during said contraction thereof wherein said reciprocating plunger drives said fluid into said pulsated stream.

28. A disposable pump for use in a hand-held pulsating jet lavage, comprising:
a tubular pump body member having a threaded outer end and a toroidally shaped chamber;
collar means mounted upon said threaded outer end;
means for introducing a sterile fluid into said chamber;
expandable means for expanding and contracting said chamber along an axis generally parallel to fluid flow in said chamber; and
said expandable means having a flange on its outer end for positive engagement with said hand-held lavage.

29. A disposable pump, as claimed in claim 28, wherein said expandable means includes:
a bellows having pleated members for urging said bellows into an expanded position.

30. A disposable pump, as claimed in claim 28, wherein said expandable means includes:
a cylinder mounted about said chamber;
piston means slidably mounted within said cylinder to close said chamber; and
means for urging said piston into an expanded position.

31. A disposable pump, as claimed in claim 28, additionally comprising:
a rigid nozzle tube inserted through said collar and against said pump body member; and
sealing means mounted about said rigid nozzle tube between said collar and said pump body member.

32. A hand-held pulsating jet lavage driven by a source of pressurized fluid to deliver a pulsed fluid from a second source, comprising:
hand-held housing means for receiving said pressurized fluid from said source;
motor means mounted within said hand-held housing means driven by said pressurized fluid;
said hand-held housing having a chamber therein;
reciprocating means driven by said motor means extending into said chamber;
disposable pump cartridge means connected to said second source of fluid;
said chamber having closure means, the opening of which permits reception of said disposable pump cartridge means;
means for engaging said disposable pump cartridge means and said reciprocating means, whereby said fluid from said source is isolated from said hand-held housing means and said pressurized fluid;
said reciprocating means including plunger means connected to said motor means having a notched end extending into said chamber; and
said disposable pump cartridge means including a flange which fits within said notched end for being positively retained therein by closure of said closure means.

33. A hand-held pulsating jet lavage driven by a source of pressurized fluid to deliver a pulsed fluid from a second source, comprising:
hand-held housing means for receiving said pressurized fluid from said source;
motor means mounted within said hand-held housing means driven by said pressurized fluid;
said hand-held housing having a chamber therein;
reciprocating means driven by said motor means extending into said chamber;
disposable pump cartridge means connected to said second source of fluid;

said chamber having closure means, the opening of which permits reception of said disposable pump cartridge means;

means for engaging said disposable pump cartridge means and said reciprocating means, whereby said fluid from said second source is isolated from said hand-held housing means and said pressurized fluid;

said motor means including means for urging said motor means and said reciprocating means into a predetermined position; and said disposable pump cartridge means including means for urging said pump means into a predetermined position, whereby said reciprocating means and said pump means are automatically aligned for reception of said pump means into said chamber.

34. A hand-held pulsating jet lavage driven by a source of pressurized fluid to deliver a pulsed fluid from a second source, comprising:

hand-held housing means for receiving said pressurized fluid from said source;

motor means mounted within said hand-held housing means driven by said pressurized fluid;

said hand-held housing having a chamber therein;

reciprocating means driven by said motor means extending into said chamber;

disposable pump cartridge means connected to said second source of fluid;

said chamber having closure means, the opening of which permits reception of said disposable pump cartridge means;

means for engaging said disposable pump cartridge means and said reciprocating means, whereby said fluid from said second source is isolated from said hand-held housing means and said pressurized fluid;

said disposable pump cartridge means including flexible tubing means for connection to said second source of fluid; and said hand-held housing means including a groove to receive said flexible tubing means.

35. A hand-held pulsating jet lavage driven by a source of pressurized fluid to deliver a pulsed fluid from a second source, comprising:

hand-held housing means for receiving said pressurized fluid from said source;

motor means mounted within said hand-held housing means driven by said pressurized fluid;

said hand-held housing having a chamber therein;

reciprocating means driven by said motor means extending into said chamber;

disposable pump cartridge means connected to said second source of fluid;

said chamber having closure means, the opening of which permits reception of said disposable pump cartridge means;

means for engaging said disposable pump cartridge means and said reciprocating means, whereby said fluid from said second source is isolated from said hand-held housing means and said pressurized fluid; and said disposable pump cartridge means including a nozzle and rigid nozzle tube wherein said motor means drives said pump means through said reciprocating means to pulse said fluid from said second source through said rigid nozzle tube and said nozzle with a sharp interface between said pulses.

36. A hand-held pulsating jet lavage for delivery of a fluid from a source of fluid, comprising:

a hand-held housing having a chamber therein;

a reciprocating plunger mounted within said housing extending into said chamber;

means for driving said plunger in a reciprocating motion;

a disposable pump removably mounted within said chamber in engagement with said plunger;

means for connecting said source of fluid to said disposable pump wherein said fluid is driven by said pump into a discrete pulsated stream by said reciprocating plunger;

said reciprocating plunger having a notched end; and said disposable pump having a flanged end portion that positively engages said notched end of said plunger.

37. A hand-held pulsating jet lavage for delivery of fluid from a source of fluid, comprising:

a hand-held housing having a chamber therein;

a reciprocating plunger mounted within said housing extending into said chamber;

means for driving said plunger in a reciprocating motion;

a disposable pump removably mounted within said chamber in engagement with said plunger;

means for connecting said source of fluid to said disposable pump wherein said fluid is driven by said pump into a pulsated stream by said reciprocating plunger;

said chamber including a closure hatch;

said plunger having a notched end extending into said chamber;

said disposable pump having a flange portion which engages said plunger notch; and said closure hatch automatically retains said pump in engagement with said plunger upon closure thereof.

38. A hand-held pulsating jet lavage for delivery of a fluid from a source of fluid, comprising:

a hand-held housing having a chamber therein;

a reciprocating plunger mounted within said housing extending into said chamber;

means for driving said plunger in a reciprocating motion;

a disposable pump removably mounted within said chamber in engagement with said plunger; and means for connecting said source of fluid to said disposable pump wherein said fluid is driven by said pump into a pulsated stream by said reciprocating plunger; and said means for driving said plunger including
a source of pressurized fluid,
a pilot valve assembly, and
a motor assembly driven by said pressurized fluid under the control of said pilot valve assembly.

39. A hand-held pulsating jet lavage for delivery of a fluid from a source of fluid, comprising:

a hand-held housing having a chamber therein;

a reciprocating plunger mounted within said housing extending into said chamber;

means for driving said plunger in a reciprocating motion;

a disposable pump removably mounted within said chamber in engagement with said plunger;

means for connecting said source of fluid to said disposable pump wherein said fluid is driven by said pump into a discrete pulsated stream by said reciprocating plunger;

a source of pressurized fluid connected to said housing;

control valve means for controlling the flow of said fluid mounted within said housing; and actuation slider means connected to said control valve means for opening said control means.

40. A hand-held pulsating jet lavage for delivery of a fluid from a source of fluid, comprising:

a hand-held housing having a chamber therein;

a reciprocating plunger mounted within said housing extending into said chamber;

means for driving said plunger in a reciprocating motion;

a disposable pump removably mounted within said chamber in engagement with said plunger;

means for connecting said source of fluid to said disposable pump wherein said fluid is driven by said pump into a discrete pulsated stream by said reciprocating plunger; and said disposable pump comprising:

a tubular pump body member having a toroidally shaped chamber, sterile means for introducing said fluid into said chamber, expandable means for expanding and contracting said chamber, said expandable means having a flange which positively engages said reciprocating plunger.

41. A disposable pump for use in a hand-held pulsating jet lavage, comprising:

a tubular pump body member having a treaded outer end and a toroidally shaped chamber;

collar means mounted upon said threaded outer end;

means for introducing a sterile fluid into said chamber;

expandable means for expanding and contracting said chamber;

said expandable means having a flange on its outer end for positive engagement with said hand-held lavage; and said expandable means comprising:

a cylinder mounted about said chamber, piston means slidably mounted within said cylinder to close said chamber, and means for urging said piston into an expanded position.

* * * * *